United States Patent [19]

Conley et al.

[11] Patent Number: 5,429,601
[45] Date of Patent: * Jul. 4, 1995

[54] ASPIRATION CONTROL SYSTEM

[75] Inventors: Paul G. Conley, St. Charles; Daniel L. Williams, Jr., St. Louis; Peter F. Appelbaum, Ballwin, all of Mo.

[73] Assignee: American Cyanamid Company, Wayne, N.J.

[*] Notice: The portion of the term of this patent subsequent to Sep. 7, 2010 has been disclaimed.

[21] Appl. No.: 105,223

[22] Filed: Aug. 11, 1993

Related U.S. Application Data

[63] Continuation-in-part of Ser. No. 834,450, Feb. 12, 1992, Pat. No. 5,242,404.

[51] Int. Cl.$^6$ ............................ A61M 31/00; A61F 9/00
[52] U.S. Cl. ............................................. 604/65; 604/51
[58] Field of Search ............................ 604/22, 26–28, 604/30, 31, 35, 65, 67, 73, 118, 119, 120, 121, 902; 606/107; 433/92

[56] References Cited

U.S. PATENT DOCUMENTS

| | | | |
|---|---|---|---|
| 3,360,185 | 12/1967 | Woolridge | 230/12 |
| 3,599,639 | 8/1971 | Spotz | 604/119 |
| 3,693,613 | 9/1972 | Kelman . | |
| 3,812,855 | 5/1974 | Banko . | |
| 3,920,014 | 11/1975 | Banko . | |
| 4,019,514 | 4/1977 | Banko . | |
| 4,024,866 | 5/1977 | Wallach . | |
| 4,168,707 | 9/1979 | Douvas et al. . | |
| 4,180,074 | 12/1979 | Murray et al. . | |
| 4,324,243 | 4/1982 | Helfgott et al. . | |
| 4,395,258 | 7/1983 | Wang et al. | 604/65 |
| 4,468,219 | 8/1984 | George et al. | 604/66 |
| 4,493,695 | 1/1985 | Cook | 604/30 |
| 4,664,601 | 5/1987 | Uchida et al. | 417/27 |
| 4,670,006 | 6/1987 | Sinnett et al. | 604/26 |
| 4,706,687 | 11/1987 | Rogers . | |
| 4,740,202 | 4/1988 | Stacey et al. | 604/119 |
| 4,757,814 | 7/1988 | Wang et al. . | |
| 4,759,349 | 7/1988 | Betz et al. . | |
| 4,770,187 | 9/1988 | Lash et al. . | |
| 4,770,654 | 9/1988 | Rogers et al. | 604/22 |
| 4,790,816 | 12/1988 | Sundblom et al. | 604/31 |
| 4,810,242 | 3/1989 | Sundblom et al. | 604/28 |
| 4,838,281 | 6/1989 | Rogers et al. . | |
| 4,898,579 | 2/1990 | Groshong et al. | 604/67 |
| 4,902,276 | 2/1990 | Zakko | 604/28 |
| 4,988,336 | 1/1991 | Kohn | 604/67 |
| 5,071,411 | 12/1991 | Hillstead | 604/246 |
| 5,195,961 | 3/1993 | Takahashi et al. | 604/35 |
| 5,242,404 | 9/1993 | Conley et al. | 604/119 |

FOREIGN PATENT DOCUMENTS

| | | | |
|---|---|---|---|
| 0121277 | 3/1984 | European Pat. Off. . | |
| 0232458 | 9/1986 | European Pat. Off. . | |
| 0362822 | 10/1989 | European Pat. Off. . | |
| 0362822 | 10/1989 | European Pat. Off. . | |
| 555625 | 8/1993 | European Pat. Off. | 604/35 |

*Primary Examiner*—Stephen C. Pellegrino
*Assistant Examiner*—Nancy Mulcare
*Attorney, Agent, or Firm*—Douglas E. Denninger

[57] ABSTRACT

An aspiration control system includes a proportional control valve and a motor, for driving a vacuum pump, which are controlled by a system controller in accordance with input commands to provide a precise, continuously variable vacuum or negative pressure within a vacuum chamber and surgical handpiece. A pressure transducer samples the vacuum output and produces a signal which is fed to the system controller. The signal is compared with an input command, and the motor speed and valve orifice size are coordinated to control the vacuum level.

19 Claims, 7 Drawing Sheets

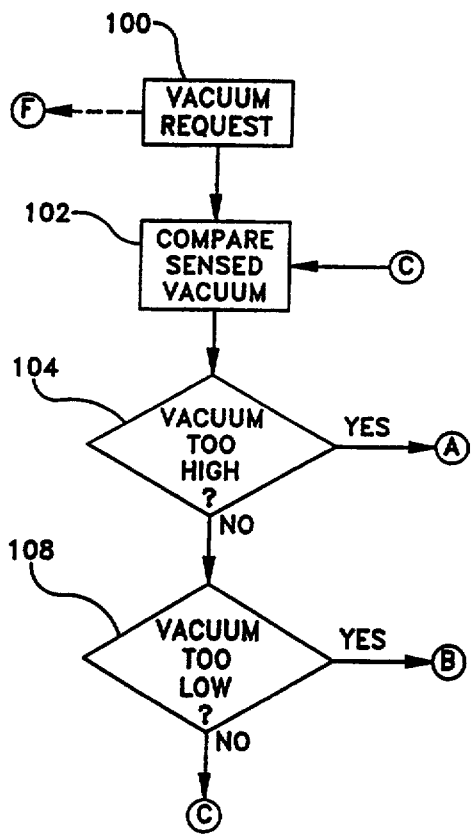
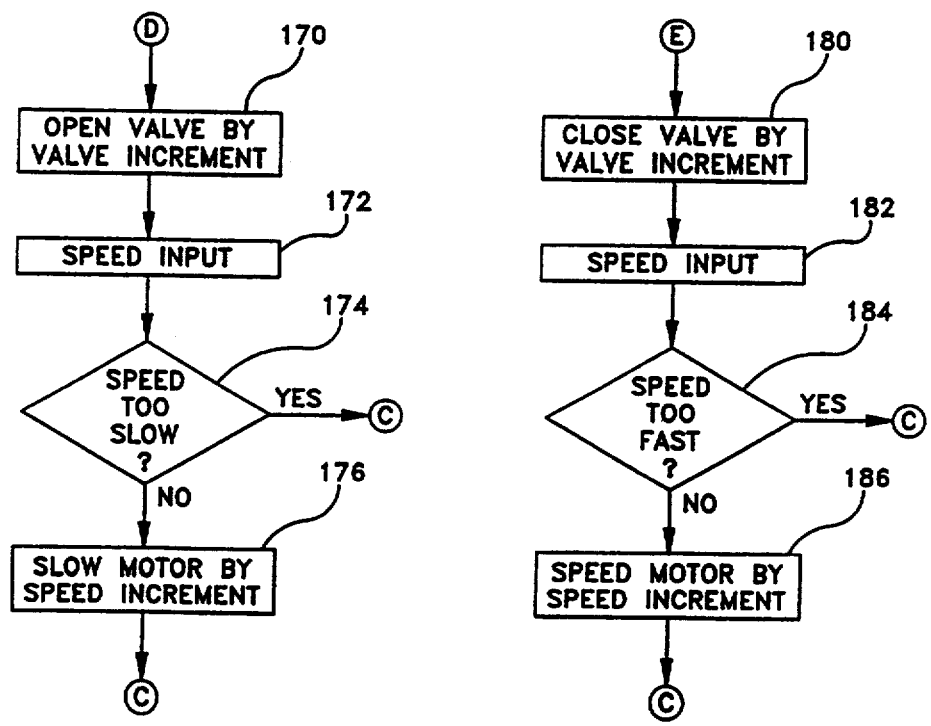

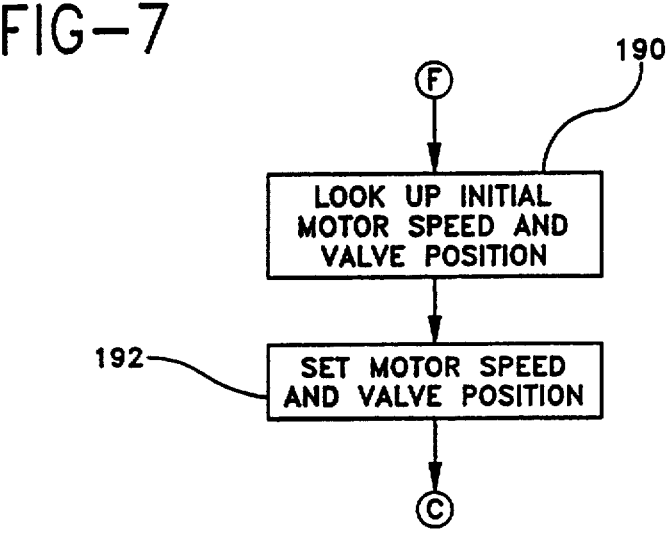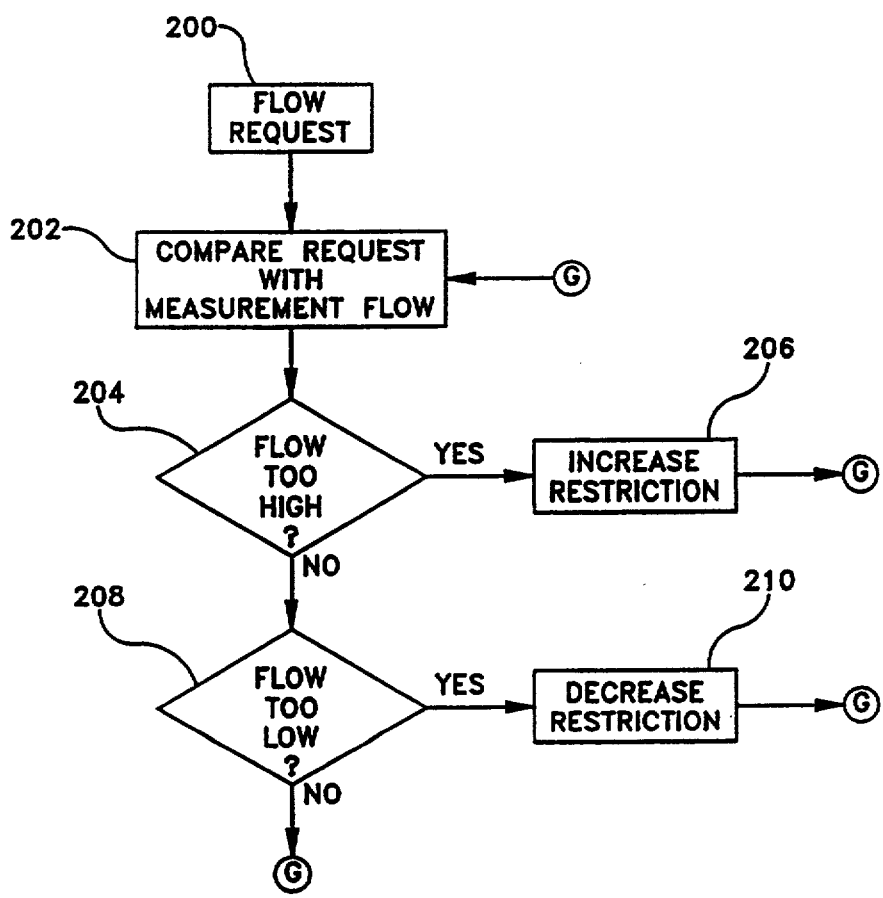

ASPIRATION CONTROL SYSTEM

RELATED APPLICATION

This application is a continuation-in-part of U.S. patent application Ser. No. 07/834,450, filed Feb. 12, 1992, now U.S. Pat. No. 5,242,404, by the same inventors hereto.

FIELD OF THE INVENTION

The present invention relates to an aspiration control system for microsurgical instruments, and in particular to an aspiration control system for use in intraocular surgery which operates a motor and a vacuum control valve in accordance with one or more commands received from a surgeon's foot control unit or a control console to accommodate various aspiration functions.

BACKGROUND OF THE INVENTION

In the field of intraocular or ophthalmic surgery, as well as in many other technical disciplines, there is a great need for an aspiration or suction system in which the vacuum or negative pressure source can be highly controlled. In ophthalmic surgery, for example, many phacoemulsification instruments use suction to aspirate the emulsified tissue away from the operative site or to allow the surgeon to "grab onto" pieces of cut tissue for manipulation within the surgical field. And, in an ophthalmic vitrectomy operation, many cutting instruments draw the tissue into the cutting edges by use of suction. In fact, the tissue removal rate or fluid flow rate is effectively controlled by the suction effect which is related directly to the negative pressure level. Thus, controlling the negative pressure level to a fine degree is highly desirable to provide the surgeon with a concomitant degree of control of the tissue removal process.

However, prior art suction devices are generally deficient in their poor control of the vacuum level or in their reliance on either an outside vacuum source or a pressurized air source. Many systems employ a pressure delivery tank in which the vacuum level is controlled by selective connection to a lower pressure source. These types of systems are characteristically underdamped pressure oscillators, in that the negative pressure level often swings wildly about the desired and often changing vacuum level. Also, the large volume of most systems causes a delay in their response, which may lead to poor user control and over-shooting of the desired vacuum level.

Many prior art systems use peristaltic pumps or diaphragm pumps to generate the desired vacuum. Examples of such systems are disclosed in U.S. Pat. Nos. 4,180,074, 3,920,014 and 4,168,707. These pump systems are sometimes noisy and are slow to generate the desired vacuum level. Further, it is desirable to have a fast response time for changes in the desired vacuum levels which is difficult to obtain with the use of a peristaltic type pump vacuum system. Such peristaltic pump systems can regulate the fluid flow out of the operative site but cannot control the vacuum level. Such pumps work by pulling the fluid versus controlling the negative pressure level. Further, the working characteristics of a peristaltic pump require use with specific tubings having a known durometer. Over time, the tubing becomes hard thereby changing the operating characteristics of the pump and the reliability of the peristaltic pump system. Furthermore, if a blockage of the aspiration needle of the surgical handpiece occurs, the peristaltic pump keeps trying to pull fluid out of the operative site thereby creating an uncontrolled vacuum rise in the tubing. Upon removal of the blockage, an aspiration surge occurs which can aspirate unintended material out of the operative site possibly causing irreparable damage to the patient's eye.

Various other prior art patents create a vacuum by use of a regulated fluid pressure which is fed through a linear solenoid valve to a venturi-type pressure vacuum converter as is shown in U.S. Pat. Nos. 4,838,281, 4,770,654, 4,810,242 and 4,706,687. The resulting vacuum is proportional to the flow through the solenoid valve and thus to a function of the current through the solenoid. However, in such vacuum systems, the regulated fluid pressure is generated by an outside air supply such as a compressor. In such cases, the compressed air is fed into the microsurgical system under pressure to the air to vacuum converter such as a venturi pump.

This technique for generating a vacuum is wasteful because it requires high rates of air flow to create the vacuum or negative pressure. And, typically the compressor is located externally from the operating area where the surgical procedure is being performed. This would also produce an additional energy waste because the compressor has to work harder to pump the compressed air through the long lengths of tubing to bring the compressed air to the operative site.

Microsurgical devices that depend on an external air pressure source to generate a vacuum are only as reliable as the external air pressure source. Such surgical devices can obviously only operate where such external air pressure sources are available and in good working order. And, while many hospitals in the United States have such external air pressure sources, individual clinics or physicians' offices may not. Further, in many foreign countries low and/or unregulated air pressure sources can disrupt the operation of such microsurgical devices.

SUMMARY OF THE INVENTION

It is, therefore, an object of the present invention to have a microsurgical system which is able to generate a controlled vacuum internally to the system in such a way as to operate on electricity only with very little waste.

A further object is to provide a more reliable microsurgical system having a vacuum delivery system that is completely independent of any outside or external air pressure source.

An additional object is to provide a vacuum delivery apparatus which includes precise vacuum control with high response throughout a selected range of vacuum pressure levels by using an electrical motor speed control.

Another object is to provide a reliable motor speed control device to control a vacuum pump based on a closed loop feedback signal from a pressure transducer to precisely control the negative air pressure without any dependency on an external or outside air pressure supply source.

A further object of the present invention is to provide a microsurgical system utilizing a vacuum delivery apparatus having a power consumption which is linearly proportional to the negative pressure required for use by the surgeon during an ophthalmic surgical operation.

And, a still further object of the present invention is to provide a microsurgical system utilizing a vacuum delivery apparatus which can supply a high negative pressure level without a high fluid flow out of the eye or operative site. The fluid flow out of the eye or operative site can be controlled independently of the vacuum pressure level.

This invention features a surgical aspiration control system including a vacuum pump, and a motor mechanically coupled to the pump, for creating a negative pressure within a vacuum chamber. A transducer, adapted for placement in pressure communication with the vacuum chamber, senses the vacuum level therein and generates a first signal representative thereof. An outlet of a proportional control valve is connected through a conduit with the vacuum pump and the vacuum chamber; an inlet of the valve communicates with a fluid at a higher pressure than the pressure within the vacuum chamber, and an orifice having a variable size is disposed between the inlet and the outlet. An appropriate vacuum level is selected through an input device such as a foot pedal or console, which generates a second signal corresponding to the appropriate level. A controller compares the first and second signals and selectively regulates the rotational speed of the motor and the size of the valve orifice to precisely control the vacuum level within the vacuum chamber and the surgical handpiece.

BRIEF DESCRIPTION OF THE DRAWINGS

Other objects, features and advantages will occur from the following description of preferred embodiments and the accompanying drawings, in which:

FIG. 4 is a flow chart of the process for adjusting vacuum level;

FIGS. 6a and 6b are flow charts of alternative operations for FIGS. 5a and 5b, respectively, in which the valve is adjusted before the motor speed is changed;

FIG. 7 is a flow chart of the implementation of initial hookup values; and

FIG. 8 is a flow chart of variable flow restriction.

DETAILED DESCRIPTION OF THE INVENTION

The present invention generally comprises an aspiration control system which features exacting control of a vacuum, that is, negative gauge pressure, which is generated and delivered to a surgical handpiece. The aspiration control system of the present invention is used as an integral part of a microsurgical system for support of eye surgeons in performing eye surgery. The microsurgical system supplies various functions needed for eye surgery and allows the surgeon to control critical parameters of each function. To implement and control the various functions, a central processing unit or system controller reads several inputs from switches and sensors to control a pneumatic system which drives surgical instruments. The system controller also reads certain inputs from the microsurgical system and converts those signals into on/off control signals to control an ultrasonic fragmentation device in a surgical handpiece for removal of cataracts or perform various other surgical operations. And, in accordance with the present invention, such a control unit also controls the aspiration control system used to aspirate cut or fragmented tissue and fluids which accumulate in the operating area during vitrectomies or cataract removal operations.

Figure 1:
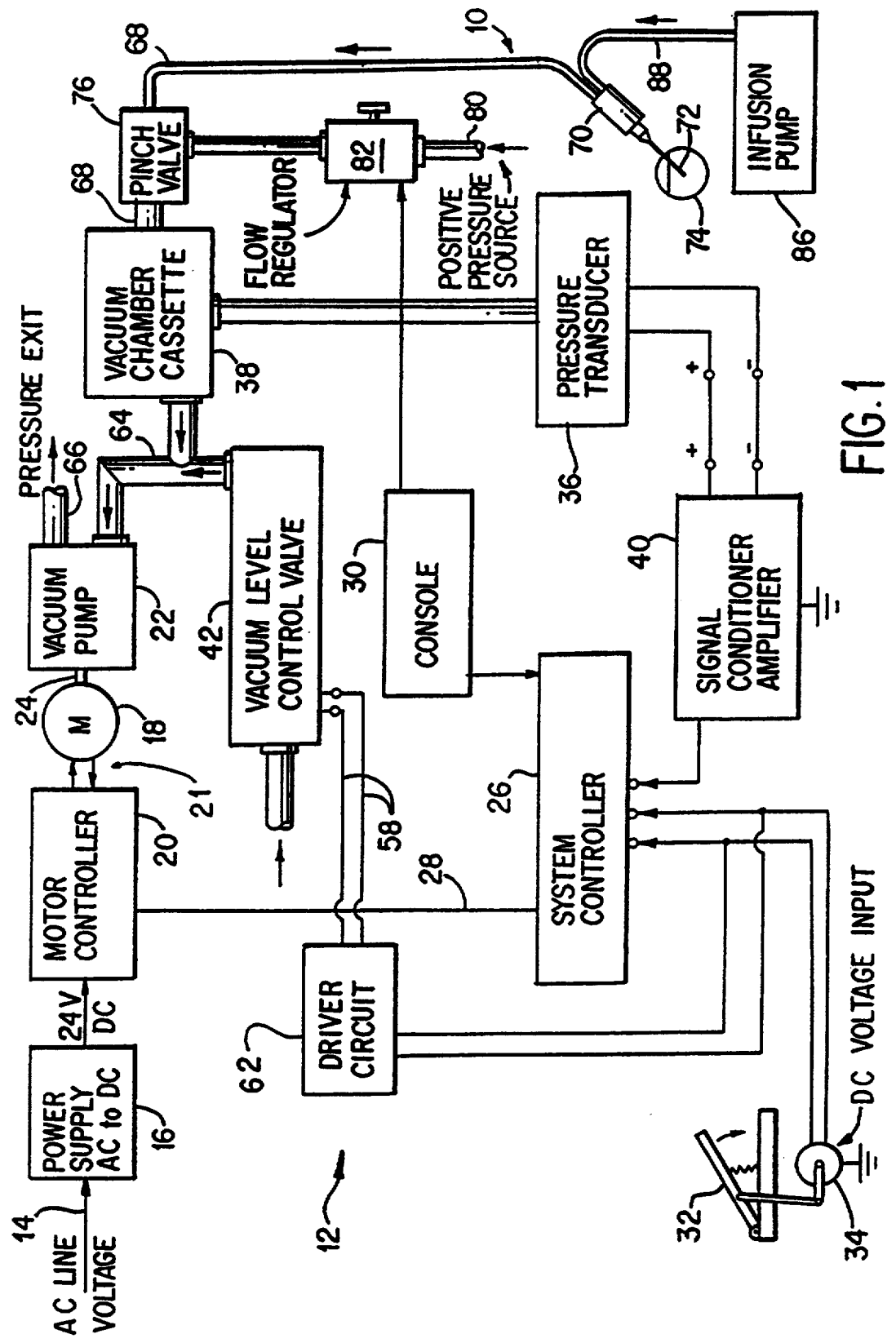
FIG. 1 is a functional block diagram of the aspiration control system of the present invention.

With reference to FIG. 1, microsurgical system 10 includes an aspiration control system 12. In the preferred embodiment, an alternating current line voltage 14 is provided to power supply 16. The power supply 16 changes the voltage from 115 volt (v) AC as supplied by the AC line voltage 14 to a 24 volt DC output to be supplied to a brushless DC motor 18 via a DC motor controller 20. The motor controller 20 receives voltage outputs from the system controller and sends output signals according to a PID (Proportional Integral Differential)-type control function to precisely regulate the speed of the brushless DC motor 18. A feedback loop 21 from the DC motor 18 to the motor controller 20 is provided to assist in the control of the DC motor's rotational speed. The feedback loop 21 provides motor speed information to the motor controller 20.

One such brushless DC motor 18 is manufactured by Fasco Industries, Inc. of St. Louis, Mo. One such motor controller 20 is manufactured by Dart Controls, Inc. of Zionsville, Ind. However, DC motor 18 and motor controller 20 could be obtained from various other sources as long as such motor 18 and motor controller 20 would operate within the parameters of the overall system. It may also be possible to integrate the separate motor controller 20 into the system controller 26 such that a separate motor controller would be unnecessary.

The system controller 26 supplies a low level control signal 28 to the motor controller 20 to adjust the speed of the motor 18. The motor 18 is connected to a rotary vane vacuum pump 22 via shaft 24. The pump 22 includes a rotatable metal hub having a plurality of sliding vanes which are moved radially outwardly by centrifugal force. Therefore, the various aspiration levels are controlled by the rotational speed of the vacuum pump 22 which is controlled by the motor controller 20 and system controller 26.

One such vacuum pump 22 as disclosed above is manufactured by Gast Manufacturing Company of Ann Arbor, Mich., as Model No. 1031-VXXX-G578. However, vacuum pump 22 could also be of a different type pump such as either a diaphragm pump, or an impeller pump, or a liquid ring impeller pump.

A user input console 30 is used to input the vacuum levels and aspiration rise time, which is the amount of time it takes the system to reach the selected vacuum level from a zero vacuum level. The console 30 feeds these commands into the system controller 26 for processing. The system controller 26 is also fed an output signal generated by an analog variable voltage device, such as a potentiometer or by a digital signal encoder 34. The potentiometer 34 is activated by a mechanical control device, such as a foot pedal 32 having a continuously variable range of angular position settings which are directly related to the potentiometer setting.

Full pedal deflection of the foot pedal 32 will give a corresponding full aspiration level as selected by the operator at the console 30. Zero pedal deflection of said foot pedal 32 will correspond to a zero aspiration level. The aspiration level is proportional to the pedal deflection. For example, if 300 mm Hg is selected by the user at the console 30 and the foot pedal 32 is depressed one-half full pedal deflection, the aspiration level achieved will be 150 mm Hg. U. S. Pat. No. 4,933,843 is incorporated herein by reference for disclosure of a footpedal and a console having one or more input keys.

A pressure transducer 36 measures the vacuum level produced in a vacuum chamber cassette 38 by the vacuum pump 22. The transducer 36 generates a signal which is fed to the system controller 26 through a signal conditioner/amplifier 40. The signal conditioner/amplifier 40 conditions the signal from the pressure transducer 36 to a level for processing by the system controller 26. The system controller 26 will compare and track the signal produced by vacuum levels sensed in the vacuum chamber cassette 38 to the input command received from the console 30 and the foot pedal deflection from foot pedal 32. The system controller 26 then sends a control signal to DC motor controller 20 to adjust the motor speed of the DC brushless motor to where the measured difference of desired vacuum and actual vacuum is zero. The vacuum chamber cassette 38 is also utilized to collect the aspirated fluid and tissue from the surgical site through a handpiece 70 as discussed below.

Figure 2A:
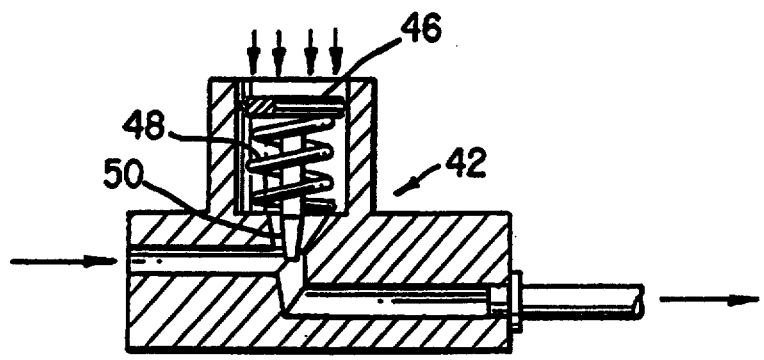
FIG. 2a is a cross-sectional elevation of a mechanically operated vacuum control valve according to one embodiment of the present invention.

A proportional vacuum level control valve 42 is utilized to provide various levels of atmospheric air flow into the vacuum pump 22. One such valve is supplied by Burket Controlmatic USA as Part No. 2832; another is supplied by Honeywell, Inc., New Brittain, Conn. as Part No. BP2E V0065. The vacuum level control valve 42 has an orifice size which can be varied and controlled by the system controller 26 to assist in the change of the vacuum level. The vacuum level is varied by the proportional control valve 42 to selectively allow air at atmospheric pressure to enter into the aspiration control system. As shown in FIG. 2a, the vacuum level control valve 42 can be controlled mechanically by a diaphragm 46 and spring 48 acting on the needle pin 50. In this embodiment, as the vacuum level changes, a corresponding change in pressure across the diaphragm 46 causes the needle pin 50 to move to increase or decrease the orifice opening accordingly to assist in achieving a certain vacuum level.

Figure 2B:
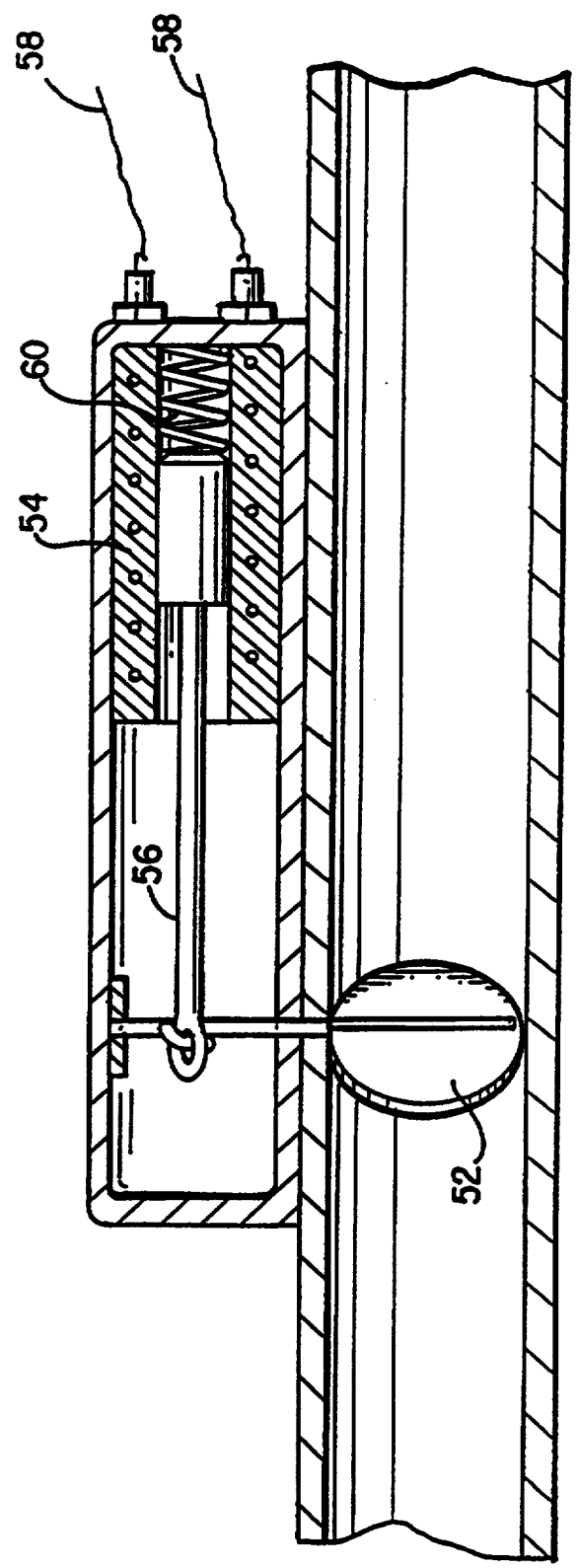
FIG. 2b is a cross-sectional elevation of an electrically operated vacuum control valve according to another embodiment of the present invention.

FIG. 2b illustrates a second embodiment of the control valve 42 having a controllable disc member 52 which is controlled by movement of a mechanical arm 56 within coil 54 in response to an electrical signal received from the system controller 26. A return spring 60 provides resistance to movement of control arm 56 and, when no current is supplied to coil 54, returns the disc member 52 to its original open position within control valve 42. In one embodiment, the control valve 42 shown in FIG. 2b and FIG. 1 is controlled by running an open loop signal from the system controller 26 through a driver circuit 62 to the electrically operated control valve 42 such that a signal from the foot pedal controller 32 via potentiometer or digital encoder 34 will act to open and close the disc member 52 of control valve 42. The driver circuit 62 acts to condition the electrical signal from foot pedal 32, via system controller 26, to the proper voltage level required by the control valve 42. As the foot pedal deflection increases, an electric signal over wires 58 will cause the mechanical arm 56 to move against the force of the return spring 60 and the pressure differential across the disc member 52 until the force induced by the coil 54 is greater than the restrictive force of the spring and the pressure differential across the disc member to move disc member 52 to change the orifice size within the control valve 42 by a predetermined amount to assist the operator in achieving various vacuum levels.

Control valve 42 allows the system to operate in the preferred speed range of the vacuum pump 22 and DC motor 18. For example, at a 3/16" diameter orifice size of valve 42, the vacuum pump will operate at its minimum specified speed (i.e. 800 rpm) without creating a vacuum or negative pressure in the vacuum cassette because air at atmospheric pressure will be allowed into the system by control valve 42. This is desirable so that upon actuation of the microsurgical system, no vacuum level will be generated in the vacuum cassette by the vacuum pump. On the other hand, to achieve a high vacuum level in the vacuum cassette, such as 650 mm Hg, the system will close down the orifice, thereby preventing any atmospheric air from entering the system, and increase the pump speed so as to obtain a high vacuum level (e.g. 650 mm Hg), which approaches a pure vacuum level of 760 mm Hg. The variable orifice size allows the system to create the higher vacuum levels without increasing the speed of the DC motor or vacuum pump to a level that could be unacceptable from a noise point of view (e.g. 55 dB).

In an alternate embodiment described in more detail below, the control valve 42 can be operated in a closed loop circuit in conjunction with the motor 18 and pump 22. This enables the system controller 26 to minimize the electrical power consumption of the motor 18 and vacuum level control valve 42 efficiently and optimally to achieve the desired vacuum level within the vacuum chamber cassette 38.

Referring to FIG. 1, it is seen that through operation of the vacuum pump 22 that a partial vacuum or negative pressure is created in the vacuum chamber cassette 38 through conduit 64. The vacuum pump 22 will exhaust air through conduit 66 either internally or externally to the cabinet (not shown) which houses all of the components of the microsurgical system. The vacuum chamber cassette 38 has another conduit 68 leading to a surgical handpiece 70 having a needle member 72 providing both liquid infusion and aspiration conduits therein for performing the various surgical procedures on an eye 74 required during a vitrectomy or cataract removal operation.

Figure 3:
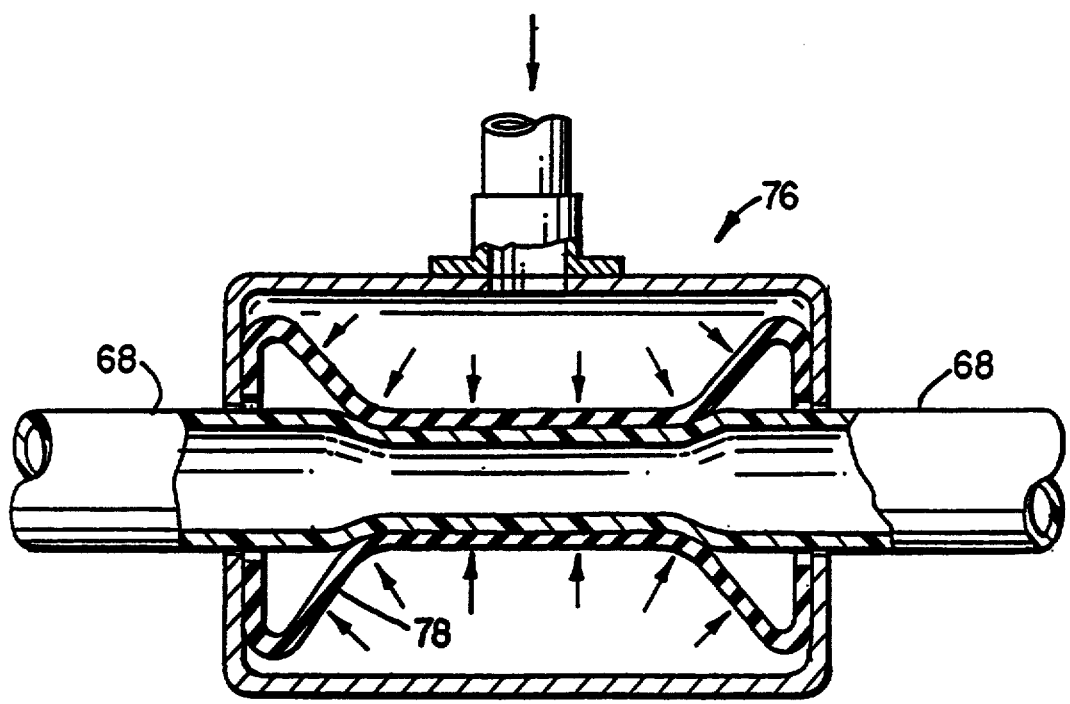
FIG. 3 is a cross-sectional elevation of the pinch valve according to the preferred embodiment of the present invention.

Due to the negative pressure created in the vacuum chamber cassette 38, the surgical handpiece will aspirate fluid out of the eye through conduit 68 during the various surgical operations. It is oftentimes desirable for the operator to variably decrease the flow of fluid being aspirated by the surgical handpiece without decreasing the vacuum level produced by vacuum pump 22. Referring to FIGS. 1 and 3, a pinch valve 76 is provided on conduit 68. Variable pinch valve 76 includes a diaphragm 78 which in response to a positive pressure source 80 variably restricts the effective area of the conduit 68 to reduce the flow of fluid through the conduit. A flow regulator 82 regulates the amount of pressurized air provided to the variable pinch valve 76 in response to an input command from the system controller 26. The greater the amount of pressurized air provided in the pinch valve, the more the diaphragm expands, further restricting the effective area of the conduit 68 and, thereby, further limiting the flow of fluid through the conduit.

One benefit of such a variable flow restrictor is that the operator can control the flow of fluid out of the eye independently of the level of vacuum or negative pressure created by the vacuum pump. This allows the operator to have a low flow rate of fluid exiting the eye while at the same time having a relatively large vacuum level available for use at the tip of the surgical handpiece for manipulating pieces of tissue within the operative site. In an alternate embodiment, it would be possible to control the flow regulator 82 via the foot pedal 32 so that the operator could change the aspirated fluid flow rate at the surgical handpiece without using his hands or relying on assistants to manipulate the controls at the console 30.

In one embodiment of the present invention, the system controller 26 consists of a PID type and a summing junction that would receive input signals from the transducer feedback signal and input commands from the console and foot pedal. The system controller thereafter would provide a control signal to the DC motor controller to precisely control the speed of the brushless DC motor. In another embodiment the system controller 26 consists of a microprocessor to provide the necessary control signal to the motor controller or DC motor.

In an alternate embodiment, the motor 18 is a three phase 115 volt electrical motor. The motor controller 20 is a three phase inverter powered by a single phase 115 volt electrical power line. The three phase inverter controls the speed and power of the three phase motor which in turn regulates the rotational speed and output of the vacuum pump 22. This embodiment would operate in a similar fashion to that discussed above. The vacuum level of the pump 22 is sampled and fed to a pressure transducer 36 which sends a feedback signal to a signal conditioner/amplifier 40 for transmission to the system controller 26. An electrical signal corresponding to the input vacuum level desired by the operator as controlled by the foot pedal controller 32 is also fed to the system controller 26. The two signals are compared in the system controller and a control signal is sent to the three phase inverter motor control 20 to change the speed of the motor 20 and thus the aspiration level as necessary. A linear relationship between the signal from the transducer 36 and the aspiration level provides a source of comparison with the operator's command signal.

The level of aspiration produced in the surgical handpiece is thus controlled by the rotational speed of the vacuum pump 22 which in turn is controlled by the frequency of the three phase voltage supplied to the motor 18 by the inverter. A vacuum level control valve 42, pinch valve 76 and flow regulator 82 could all be provided as discussed in more detail below.

In one construction, the microsurgical system 10 further includes an infusion pump system 86 for providing the surgical handpiece 70 with fluid irrigation through conduit 88 to assist the operator in the various ophthalmic surgical procedures required in vitrectomies or cataract removal operations.

Figure 5A:
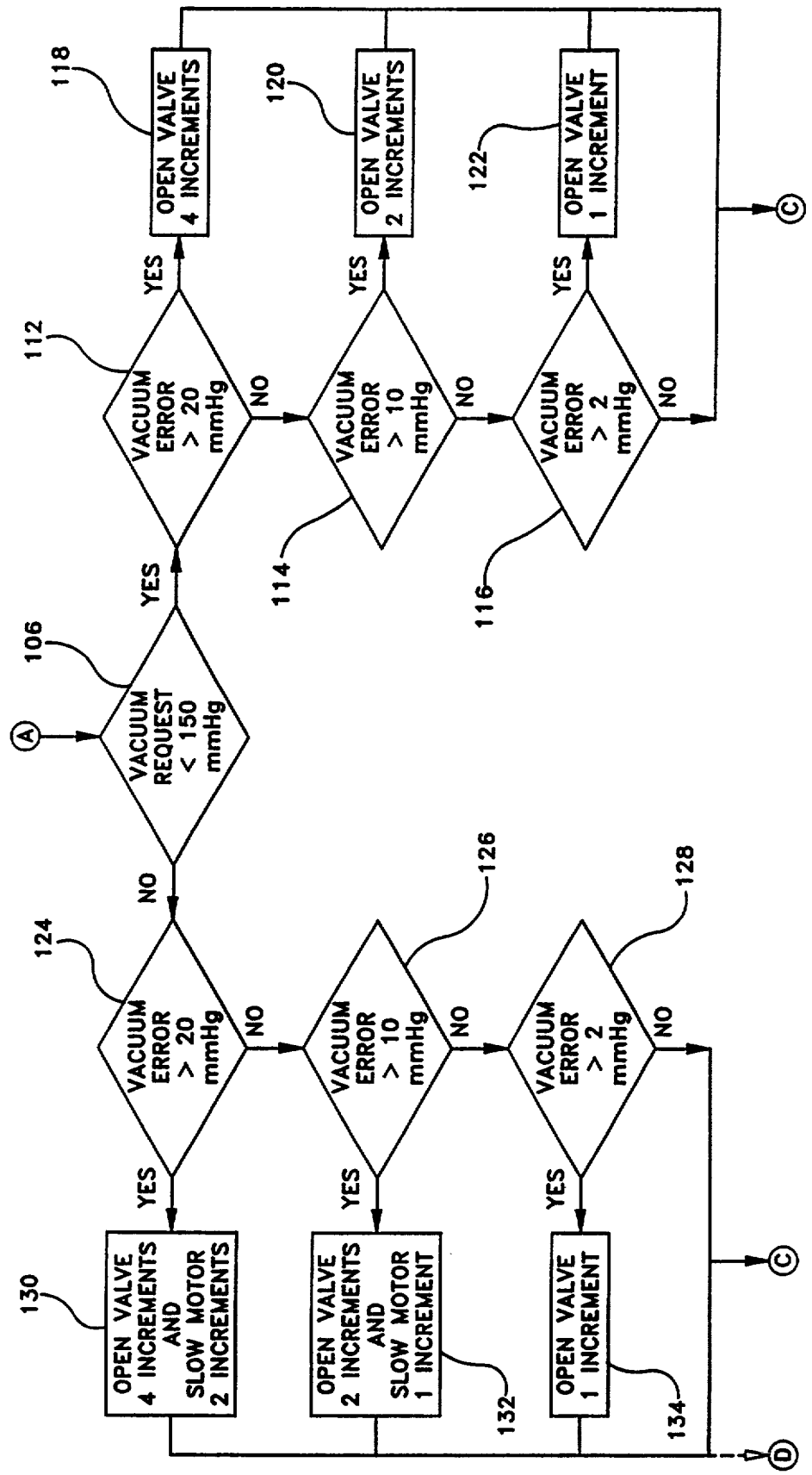
FIG. 5a is a more detailed flow chart of the operation to reduce vacuum level.
Figure 5B:
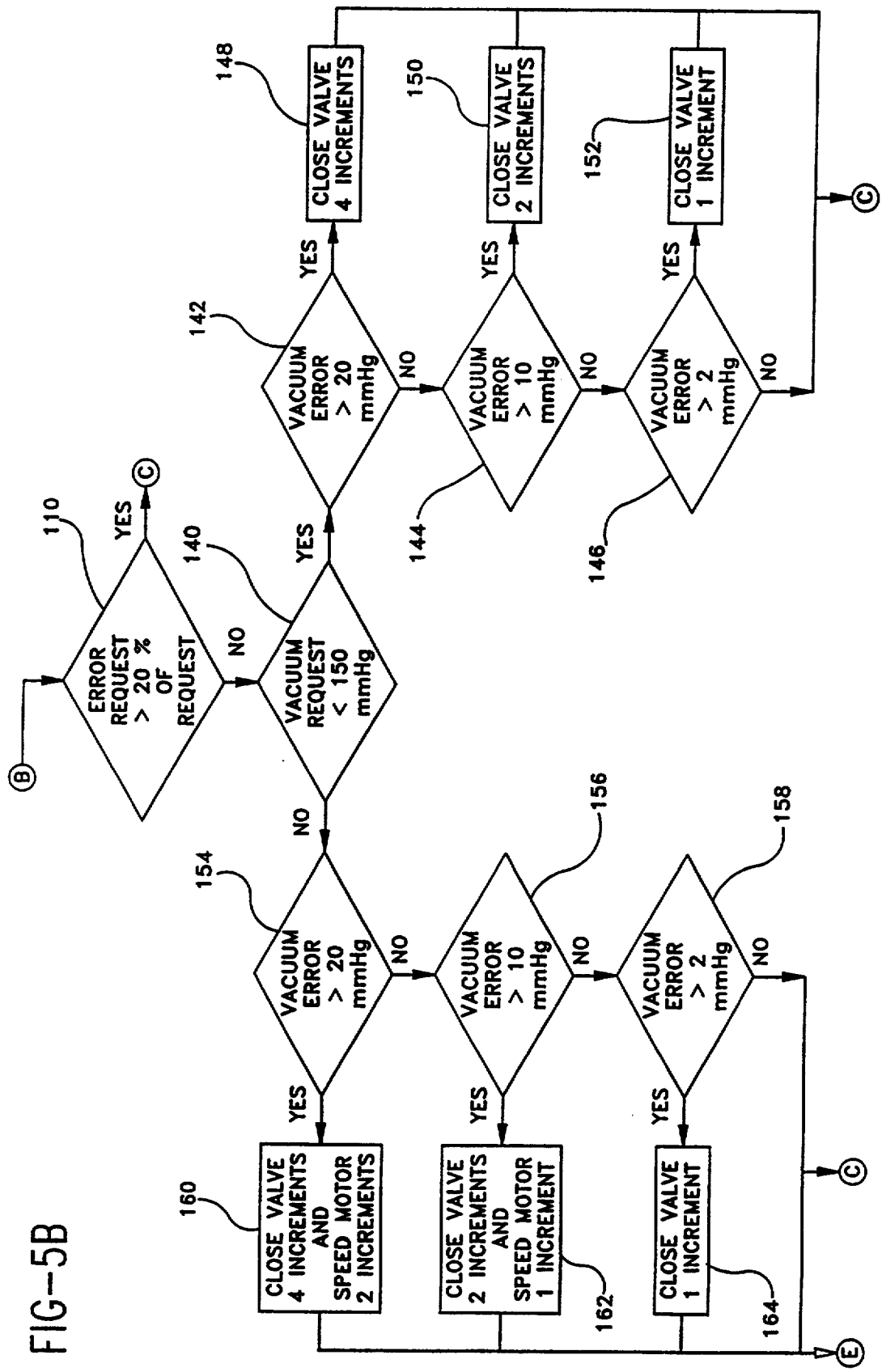
FIG. 5b is a flow chart of the operation to decrease vacuum level as determined in FIG. 4.

In preferred constructions, the aspiration control system 12, FIG. 1, operates as illustrated in FIGS. 4–5B. A vacuum request, step 100, is made through the console 30 or the footpedal 32, and is compared with a sensed vacuum level, step 102, as determined by the pressure transducer 36. If the measured difference, that is, the vacuum error, between the requested and the sensed vacuum levels indicates that the sensed vacuum level is too high, step 104, the operation proceeds to step 106, FIG. 5A. If the sensed vacuum is too low, step 108, the operation proceeds to step 110, FIG. 5B. Otherwise, the operation returns to step 102 to repeat the comparison.

When the sensed vacuum is too high and the vacuum request is less than 150 mmHg, step 106, FIG. 5A, the operation proceeds to steps 112, 114 or 116, depending on the magnitude of the vacuum error. If the error is greater than 20 mmHg, the control valve 42 is commanded to open four increments, step 118. An error greater than 10 mmHg leads to valve 42 being opened two increments, step 120, and an error less than that but greater than 2 mmHg results in valve 42 being opened one increment, step 122. The motor speed remains unchanged in all three cases, and operation returns to step 102, FIG. 4.

If the vacuum request is greater than 150 mmHg, the operation proceeds to steps 124, 126, or 128, FIG. 5A, again depending on the magnitude of the vacuum error. When the vacuum request is greater than 150 mmHg, the control valve 42 typically is largely closed. The speed of motor 18 therefore must be adjusted as well.

An error greater than 20 mmHg prompts the controller 26 to command the valve 42 to be opened four increments and the motor 18 to be slowed by two increments, step 130. If the error is greater than 10 mmHg, valve 42 is opened two increments and the motor 18 is slowed by one increment, step 132. A lower vacuum error greater than 2 mmHg results in valve 42 being opened one increment, and motor speed is maintained. Operation returns to step 102, FIG. 4 in the construction; in an alternate construction, operation proceeds to the routine illustrated in FIG. 6A, described below.

When the sensed vacuum is too low, controller 26 determines whether the vacuum error is less than twenty percent of the vacuum request, step 110, FIG. 5B. If greater, the operation immediately returns to step 102, FIG. 4; no correction is attempted, because an abnormal condition is presumed, such as sudden removal of the tip 72 of the instrument 70 from the eye 74.

Once the vacuum error is twenty percent or less of the vacuum request, the controller 26 determines whether the vacuum request is less than 150 mmHg, step 140. If it is less, the vacuum error is evaluated as greater than 20 mmHg, step 142, 10 mmHg, step 144, or 2 mmHg, step 146. Control valve 42 then is commanded to close four increments, step 148, two increments, step 150, or one increment, step 152, respectively, and operation returns to step 102, FIG. 4.

A vacuum request greater than 150 mmHg prompts vacuum error evaluation at greater than 20 mmHg, step 154, 10 mmHg, step 156, or 2 mmHg, step 158. Valve 42 then is commanded to close four increments and motor speed is slowed two increments, step 160, valve 42 is closed two increments and motor speed is slowed one increment, step 162, or valve 42 is closed one increment, step 164, respectively. Operation returns to step 102, FIG. 4.

In an alternative construction, control valve 42 is adjusted prior to changing the speed of motor 18. For steps 130, 132, 134, FIG. 5A, valve 42 is opened by the respective valve increment, step 170, FIG. 6A, and the present motor speed is input, step 172, as determined from motor feedback signal 21 which is fed to controller 26. If the motor speed is already lower than desired, step 174, such as when a large load is placed on motor 18, the operation proceeds to step 102, FIG. 4, without further lowering the speed. Otherwise, speed is lowered by the appropriate increment, step 176.

Similarly, steps 160, 162, 164, FIG. 5B, may include initial valve closure, step 180, FIG. 6B, followed by speed input, step 182, speed evaluation, step 184, and speed incrementation, step 186, as long as the motor speed is not too fast.

It is desirable to operate motor 18 above a minimum speed, e.g. 800 rpm, to enable rapid response to a speed change command. Operating the motor 18 below its maximum speed and setting the control valve 42 between a fully open and a fully closed orifice size enhances versatility in responding to changes in the requested vacuum level and to varying loads. Also, it is desirable to provide some air into cassette 38 through the control valve 42 to avoid placing an excess load on the motor 18. The operation of valve 42 and the motor 18, therefore, is coordinated to optimize performance of the microsurgical system 10.

System controller 26 preferably is initialized as illustrated in FIG. 7. An initial valve orifice size and motor speed are determined, step 190, based on Tables I and II below.

TABLE I

| Valve Increments | Vacuum Level (mmHg) |
|---|---|
| 4095 | 0 |
| 2010 | 10 |
| 1790 | 20 |
| 1282 | 50 |
| 1076 | 100 |
| 973 | 200 |
| 827 | 300 |

TABLE II

| Speed Increments | Vacuum Level (mmHg) |
|---|---|
| 0 | 0 |
| 2300 | 10 |
| 2410 | 20 |
| 2500 | 50 |
| 2500 | 100 |
| 2664 | 200 |
| 2733 | 300 |

Table values of 4095 represent a fully opened valve 42, Table I, and maximum motor speed, Table II.

Preferably, system controller 26 also commands variable flow restriction such as through flow regulator 82. A desired flow request, step 200, FIG. 8, is compared with measured flow, step 202. If flow is too high, step 204, restriction of the second conduit 68 is increased, step 206. If flow is too low, step 208, restriction is decreased, step 210. Operation cycles to step 202.

While the invention has been described in terms of the embodiments described above, it will be apparent to those skilled in the art that numerous modifications can be made such as the type of vacuum pump or system controller utilized to perform the basic functions of the aspiration control system. All such modifications falling within the spirit of the invention are intended to be covered by the claims set out below.

Although specific features of the invention are shown in some drawings and not in others, this is for convenience only as each feature may be combined with any or all of the other features in accordance with the invention.

What is claimed is:

1. A surgical aspiration control system for aspirating fluid and cut tissue from an operative site through a fluid conduit from a surgical handpiece into a vacuum chamber, the system comprising:
   a vacuum pump for creating a negative pressure with the vacuum chamber, said vacuum pump being connectable in fluid communication to the vacuum chamber;
   a motor mechanically coupled to said vacuum pump for operating said vacuum pump;
   transducer means adapted for placement in pressure communication with the vacuum chamber, for sensing the vacuum within the vacuum chamber and for generating a first signal in response thereto;
   a proportional control valve having an orifice which is variable in size and is disposed between a valve inlet and a valve outlet, said valve inlet communicatable with a fluid at a higher pressure than the pressure within the vacuum chamber, and said valve outlet being connectable in fluid communication to the vacuum chamber;
   input means for selecting an appropriate vacuum level for aspirating and cutting tissue and for generating a second signal which corresponds to said appropriate level; and
   controller means, connected to said transducer means and said input means, for comparing the first and second signals and for selectively regulating the rotational speed of said motor and the size of said orifice of said control valve to precisely control the vacuum level within the vacuum chamber and the surgical handpiece.

2. The surgical aspiration control system of claim 1 wherein said input means includes a foot pedal having a continuously variable range of angular position settings to enable selection of the appropriate vacuum level.

3. The surgical aspiration control system of claim 1 wherein said input means includes a console having at least one key to enable selection of the appropriate vacuum level.

4. The surgical aspiration control system of claim 1 wherein said control valve includes a diaphragm and spring acting on a needle pin such that as the vacuum level changes in the vacuum chamber, a corresponding change in atmospheric pressure across the diaphragm causes the needle pin to increase or decrease said orifice size.

5. The surgical aspiration control system of claim 1 wherein said control valve includes an electrically controllable valve member.

6. The surgical aspiration control system of claim 1 further including a pinch valve means installable on the fluid conduit between the vacuum chamber and the surgical handpiece to restrict the flow of fluid being aspirated by the surgical handpiece into the vacuum chamber in response to a command from said controller means.

7. The surgical aspiration control system of claim 6 wherein said pinch valve means comprises:
   a positive pressure source;
   a valve means having a diaphragm which in response to the positive pressure source restricts the effective area of the fluid conduit between the surgical handpiece and vacuum chamber; and
   a flow regulator which regulates the amount of pressurized air provided from the positive pressure source to the diaphragm within the valve in response to the command from the controller means such that the fluid flow being aspirated through the surgical handpiece can be controlled independent of the vacuum level within the vacuum chamber.

8. The surgical aspiration control system of claim 1 wherein said motor is a brushless DC motor.

9. The surgical aspiration control system of claim 8 wherein said motor further comprises a motor controller having a PID type controller receiving a control signal from said controller means and sending a second control signal to said motor to precisely regulate the rotational speed and output of said motor and vacuum pump.

10. The surgical aspiration control system of claim 9 wherein said motor controller receives a feedback signal from said motor to precisely control the speed of said motor.

11. The surgical aspiration control system of claim 1 wherein said vacuum pump is a rotary vane vacuum pump.

12. The surgical aspiration control system of claim 1 further including a second conduit adapted to connect said vacuum pump to the vacuum chamber in fluid communication, and being further adapted to connect said valve outlet of said proportional control valve to the vacuum chamber in fluid communication.

13. The surgical aspiration control system of claim 12 further including the vacuum chamber, said vacuum chamber being removably connected to said second conduit.

14. The surgical aspiration control system of claim 13 wherein said vacuum chamber includes a removable cassette having rigid walls and a constant volume.

15. A surgical aspiration control system for aspirating fluid and cut tissue from an operative site through a fluid conduit from a surgical handpiece into a vacuum chamber, the system comprising:
- a vacuum pump for creating a negative pressure within the vacuum chamber, said vacuum pump being connectable in fluid communication to the vacuum chamber;
- a motor mechanically coupled to said vacuum pump for operating said vacuum pump;
- transducer means adapted for placement in pressure communication with the vacuum chamber, for sensing the vacuum within the vacuum chamber and for generating a first signal in response thereto;
- a proportional control valve having an orifice which is variable in size and is disposed between a valve inlet and a valve outlet, said valve inlet communicatable with a fluid at a higher pressure than the pressure within the vacuum chamber, and said valve outlet being connectable in fluid communication to the vacuum chamber;
- a console having at least one key to enable selection of a maximum vacuum level;
- a foot pedal having a continuously variable range of angular position settings to enable selection of an appropriate vacuum level, no greater than said maximum vacuum level, for aspirating and cutting tissue and for generating a second signal which corresponds to said appropriate level; and
- controller means, connected to said transducer means and said input means, for comparing the first and second signals and for selectively regulating the rotational speed of said motor and the size of said orifice of said control valve to precisely control the vacuum level within the vacuum chamber and the surgical handpiece by driving a measured difference between the first and second signals toward zero.

16. The surgical aspiration control system of claim 15 further including a second conduit adapted to connect said vacuum pump to the vacuum chamber in fluid communication, and being further adapted to connect said valve outlet of said proportional control valve to the vacuum chamber in fluid communication.

17. The surgical aspiration control system of claim 16 further including the vacuum chamber, said vacuum chamber being removably connected to said second conduit.

18. The surgical aspiration control system of claim 17 wherein said vacuum chamber includes a removable cassette having rigid walls and a constant volume.

19. A method for controlling a surgical aspiration system for aspirating fluid and cut tissue from an operative site through a surgical handpiece into a vacuum chamber, comprising:
- providing a proportional control valve having a variable orifice size, a vacuum pump, and a motor for driving the vacuum pump;
- connecting the vacuum pump to the vacuum chamber for creating a negative pressure level within the vacuum chamber, the vacuum chamber being in fluid communication with the surgical handpiece;
- connecting the control valve between the vacuum chamber and the vacuum pump;
- producing a first signal corresponding to the negative pressure level within the vacuum chamber;
- producing a second signal corresponding to the desired negative pressure within the vacuum chamber;
- comparing the first and second signals; and
- producing a third, control signal to selectively control the speed of the motor and a fourth, control signal to selectively control the orifice size of the control valve to regulate the negative pressure level within the vacuum chamber, the control signals corresponding to the comparison of the first and second signals.

* * * * *